(12) United States Patent
Yin et al.

(10) Patent No.: US 12,190,888 B2
(45) Date of Patent: Jan. 7, 2025

(54) SYSTEM AND METHOD FOR SECURE TRAINING OF SPEECH PROCESSING SYSTEMS

(71) Applicant: Nuance Communications, Inc., Burlington, MA (US)

(72) Inventors: Shou-Chun Yin, Brossard (CA); Junho Park, Bedford, MA (US); Dushyant Sharma, Tracy, CA (US); DoYeong Kim, Lexington, MA (US); Francesco Nespoli, London (GB)

(73) Assignee: Microsoft Technology Licensing, LLC, Redmond, WA (US)

( * ) Notice: Subject to any disclaimer, the term of this patent is extended or adjusted under 35 U.S.C. 154(b) by 297 days.

(21) Appl. No.: 17/840,795

(22) Filed: Jun. 15, 2022

(65) Prior Publication Data

US 2023/0410814 A1  Dec. 21, 2023

(51) Int. Cl.
*G10L 15/26* (2006.01)
*G10L 13/04* (2013.01)
*G10L 15/06* (2013.01)

(52) U.S. Cl.
CPC .............. *G10L 15/26* (2013.01); *G10L 13/04* (2013.01); *G10L 15/063* (2013.01)

(58) Field of Classification Search
CPC ........ G10L 13/04; G10L 15/063; G10L 15/26
See application file for complete search history.

(56) References Cited

U.S. PATENT DOCUMENTS

| | | | | |
|---|---|---|---|---|
| 2013/0266127 A1* | 10/2013 | Schachter | ............... | G10L 25/48 379/88.01 |
| 2014/0278426 A1 | 9/2014 | Jost et al. | | |
| 2019/0088254 A1* | 3/2019 | Filar | ............... | G06F 40/295 |
| 2021/0110813 A1* | 4/2021 | Khoury | ............... | G06N 3/0464 |
| 2021/0118425 A1 | 4/2021 | Pollet et al. | | |
| 2021/0125615 A1* | 4/2021 | Medalion | ............... | G06N 3/044 |
| 2021/0241777 A1* | 8/2021 | Bladsy | ............... | G10L 17/02 |
| 2021/0270171 A1* | 9/2021 | Johnson | ............... | F15D 1/009 |
| 2022/0059121 A1* | 2/2022 | Rao | ............... | G10L 25/60 |
| 2023/0259653 A1* | 8/2023 | Lane | ............... | G10L 21/06 726/27 |

OTHER PUBLICATIONS

"International Search Report and Written Opinion issued in PCT Application No. PCT/US23/022815", Mailed Date: Aug. 8, 2023, 8 Pages.

* cited by examiner

*Primary Examiner* — Eric Yen
(74) *Attorney, Agent, or Firm* — Brian J. Colandreo; Heath M. Sargeant; Holland & Knight LLP (57) ABSTRACT

A method, computer program product, and computing system for generating an obscured speech signal from an input speech signal and an obscured transcription from a transcription of the input speech signal. A speaker embedding may be extracted from the input speech signal. A speaker embedding delta may be generated based upon, at least in part, the extracted speaker embedding and a synthetic speaker embedding. A synthetic speech signal may be generated from the obscured speech signal using the synthetic speaker embedding. A residual signal may be generated based upon, at least in part, the obscured speech signal and the speaker embedding delta. A speech processing system may be trained using the obscured transcription, the synthetic speech signal, the speaker embedding delta, and the residual signal.

20 Claims, 6 Drawing Sheets

SYSTEM AND METHOD FOR SECURE TRAINING OF SPEECH PROCESSING SYSTEMS

BACKGROUND

Ambient Cooperative Intelligence (ACI) may be used, e.g., to turn transcribed conversational (e.g., physician, patient, and/or other participants such as patient's family members, nurses, physician assistants, etc.) speech into formatted (e.g., medical) reports. Such reports may be reviewed, e.g., to assure accuracy of the reports by the physician, scribe, etc. Further, such automatically generated conversational data may be used in combination with audio encounter information to train a machine-based speech processing system or model to more accurately convert audio encounter information to a textual representation. Training such systems requires a large collection of labeled training data (e.g., audio data and corresponding text transcriptions). This data is usually stored for considerable periods of time for training various speech processing systems.

However, storing audio encounter information and corresponding text transcriptions for training a speech processing system may present a security concern. Conventional approaches exploit text-to-speech that require estimation of speaker and background acoustic information and do not accurately reconstruct the audio required for training of speech processing systems. As such, these conventional approaches that seek to securely access and utilize audio encounter information and corresponding textual data for training speech processing systems result in less accurate speech processing (i.e., increased word error rate in machine-based speech processing).

BRIEF DESCRIPTION OF THE DRAWINGS

Like reference symbols in the various drawings indicate like elements.

DETAILED DESCRIPTION OF THE PREFERRED EMBODIMENTS

As discussed above, processing and storing audio encounter information and corresponding transcriptions for training a speech processing system or model present a security concern. For example, sensitive content may be obtained by a breach. For example, an internal actor could potentially scan lots of internal data (e.g., by looking for particular persons or classes of information, such as credit card numbers). However, just removing or obscuring sensitive content may result in degraded speech processing system performance. For example and as discussed above, conventional approaches that seek to obscure audio encounter information and corresponding textual data using text-to-speech systems result in less accurate speech processing (i.e., increased word error rate in machine-based speech processing).

As will be discussed in greater detail below, implementations of the present disclosure provide a technical solution necessarily rooted in computing technology to provide secure training of speech processing systems or models. Specifically, implementations of the present disclosure may generate a secure representation of the audio encounter information that accounts for acoustic properties (i.e., background noise, reverberation, etc.) within the audio encounter information to train speech processing systems without exposing sensitive content. In this manner, implementations of the present disclosure may utilize text-to-speech and voice style transfer (VST) processing to generate obscured or "de-identified" data and a residual signal that may be stored separately. The de-identified data and the residual signal may allow for reconstruction of the original signal (to facilitate high accuracy speech processing model training). Additionally, implementations of the present disclosure may provide for content obscuring awareness during training to make the training of the speech processing system more robust to mismatch between actual audio encounter information and synthetically obscured audio information.

The details of one or more implementations are set forth in the accompanying drawings and the description below. Other features and advantages will become apparent from the description, the drawings, and the claims.

Figure 1:
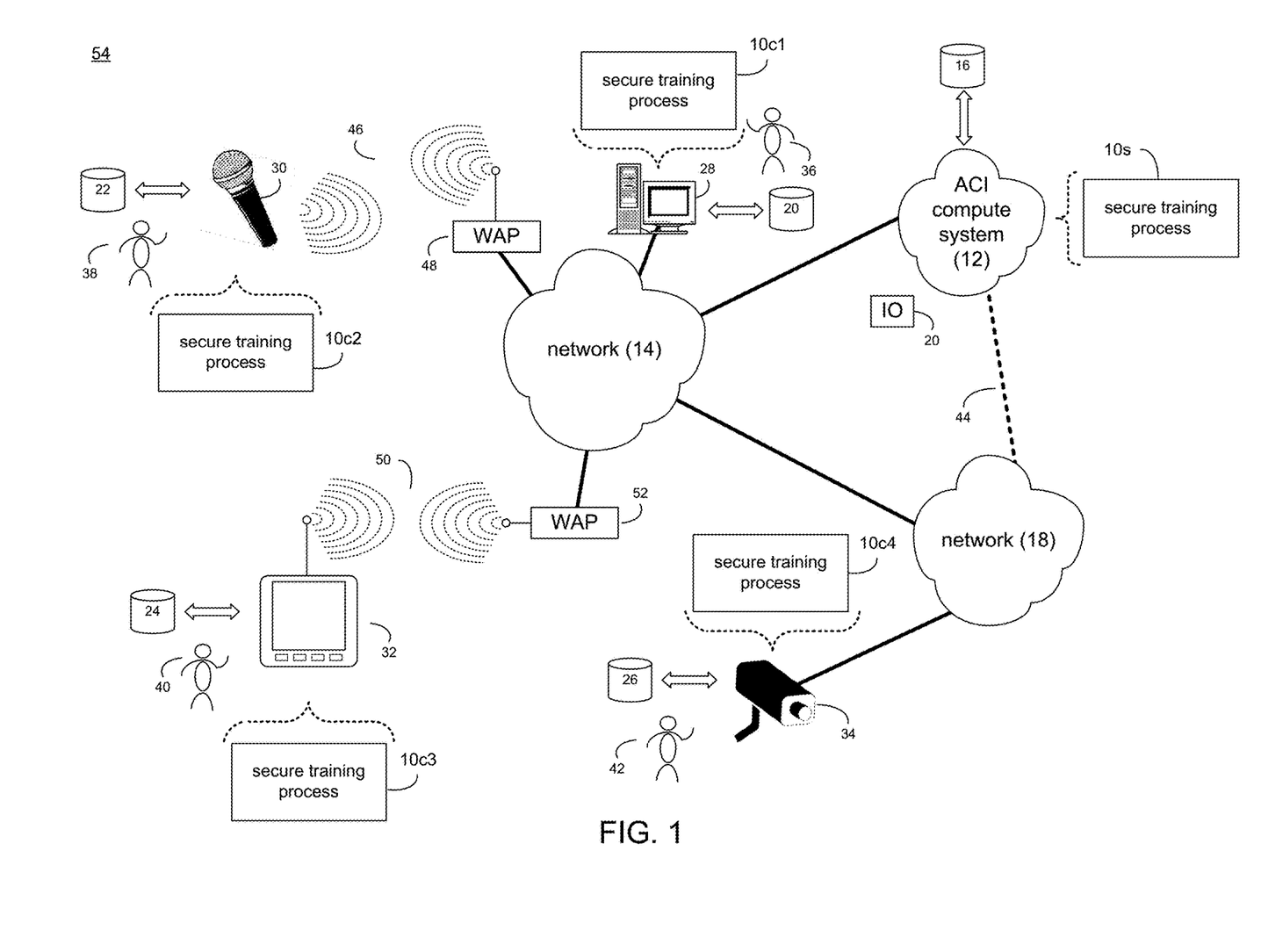
FIG. 1 is a diagrammatic view of an automated clinical documentation computer system and a secure training process coupled to a distributed computing network.

System Overview:

Referring to FIG. 1, there is shown secure training process 10. Secure training process 10 may be implemented as a server-side process, a client-side process, or a hybrid server-side/client-side process. For example, secure training process 10 may be implemented as a purely server-side process via secure training process 10s. Alternatively, secure training process 10 may be implemented as a purely client-side process via one or more of secure training process 10c1, secure training process 10c2, secure training process 10c3, and secure training process 10c4. Alternatively still, secure training process 10 may be implemented as a hybrid server-side/client-side process via secure training process 10s in combination with one or more of secure training process 10c1, secure training process 10c2, secure training process 10c3, and secure training process 10c4.

Accordingly, secure training process 10 as used in this disclosure may include any combination of secure training process 10s, secure training process 10c1, secure training process 10c2, secure training process 10c3, and secure training process 10c4.

Secure training process 10s may be a server application and may reside on and may be executed by automated clinical documentation (ACI) computer system 12, which may be connected to network 14 (e.g., the Internet or a local area network). ACI computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

As is known in the art, a SAN may include one or more of a personal computer, a server computer, a series of server computers, a mini computer, a mainframe computer, a RAID device and a NAS system. The various components of ACI computer system 12 may execute one or more operating systems, examples of which may include but are not limited to: Microsoft Windows Server™; Redhat Linux™, Unix, or a custom operating system, for example.

The instruction sets and subroutines of secure training process 10s, which may be stored on storage device 16 coupled to ACI computer system 12, may be executed by one or more processors (not shown) and one or more memory architectures (not shown) included within ACI computer system 12. Examples of storage device 16 may include but are not limited to: a hard disk drive; a RAID device; a random access memory (RAM); a read-only memory (ROM); and all forms of flash memory storage devices.

Network 14 may be connected to one or more secondary networks (e.g., network 18), examples of which may include but are not limited to: a local area network; a wide area network; or an intranet, for example.

Various IO requests (e.g. IO request 20) may be sent from secure training process 10s, secure training process 10c1, secure training process 10c2, secure training process 10c3 and/or secure training process 10c4 to ACI computer system 12. Examples of IO request 20 may include but are not limited to data write requests (i.e. a request that content be written to ACI computer system 12) and data read requests (i.e. a request that content be read from ACI computer system 12).

The instruction sets and subroutines of secure training process 10c1, secure training process 10c2, secure training process 10c3 and/or secure training process 10c4, which may be stored on storage devices 20, 22, 24, 26 (respectively) coupled to ACI client electronic devices 28, 30, 32, 34 (respectively), may be executed by one or more processors (not shown) and one or more memory architectures (not shown) incorporated into ACI client electronic devices 28, 30, 32, 34 (respectively). Storage devices 20, 22, 24, 26 may include but are not limited to: hard disk drives; optical drives; RAID devices; random access memories (RAM); read-only memories (ROM), and all forms of flash memory storage devices. Examples of ACI client electronic devices 28, 30, 32, 34 may include, but are not limited to, personal computing device 28 (e.g., a smart phone, a personal digital assistant, a laptop computer, a notebook computer, and a desktop computer), audio input device 30 (e.g., a handheld microphone, a lapel microphone, an embedded microphone (such as those embedded within eyeglasses, smart phones, tablet computers and/or watches) and an audio recording device), display device 32 (e.g., a tablet computer, a computer monitor, and a smart television), machine vision input device 34 (e.g., an RGB imaging system, an infrared imaging system, an ultraviolet imaging system, a laser imaging system, a SONAR imaging system, a RADAR imaging system, and a thermal imaging system), a hybrid device (e.g., a single device that includes the functionality of one or more of the above-references devices; not shown), an audio rendering device (e.g., a speaker system, a headphone system, or an earbud system; not shown), various medical devices (e.g., medical imaging equipment, heart monitoring machines, body weight scales, body temperature thermometers, and blood pressure machines; not shown), and a dedicated network device (not shown).

Users 36, 38, 40, 42 may access ACI computer system 12 directly through network 14 or through secondary network 18. Further, ACI computer system 12 may be connected to network 14 through secondary network 18, as illustrated with link line 44.

The various ACI client electronic devices (e.g., ACI client electronic devices 28, 30, 32, 34) may be directly or indirectly coupled to network 14 (or network 18). For example, personal computing device 28 is shown directly coupled to network 14 via a hardwired network connection. Further, machine vision input device 34 is shown directly coupled to network 18 via a hardwired network connection. Audio input device 30 is shown wirelessly coupled to network 14 via wireless communication channel 46 established between audio input device 30 and wireless access point (i.e., WAP) 48, which is shown directly coupled to network 14. WAP 48 may be, for example, an IEEE 802.11a, 802.11b, 802.11g, 802.11n, Wi-Fi, and/or Bluetooth device that is capable of establishing wireless communication channel 46 between audio input device 30 and WAP 48. Display device 32 is shown wirelessly coupled to network 14 via wireless communication channel 50 established between display device 32 and WAP 52, which is shown directly coupled to network 14.

The various ACI client electronic devices (e.g., ACI client electronic devices 28, 30, 32, 34) may each execute an operating system, examples of which may include but are not limited to Microsoft Windows™, Apple Macintosh™, Redhat Linux™, or a custom operating system, wherein the combination of the various ACI client electronic devices (e.g., ACI client electronic devices 28, 30, 32, 34) and ACI computer system 12 may form modular ACI system 54.

Figure 2:
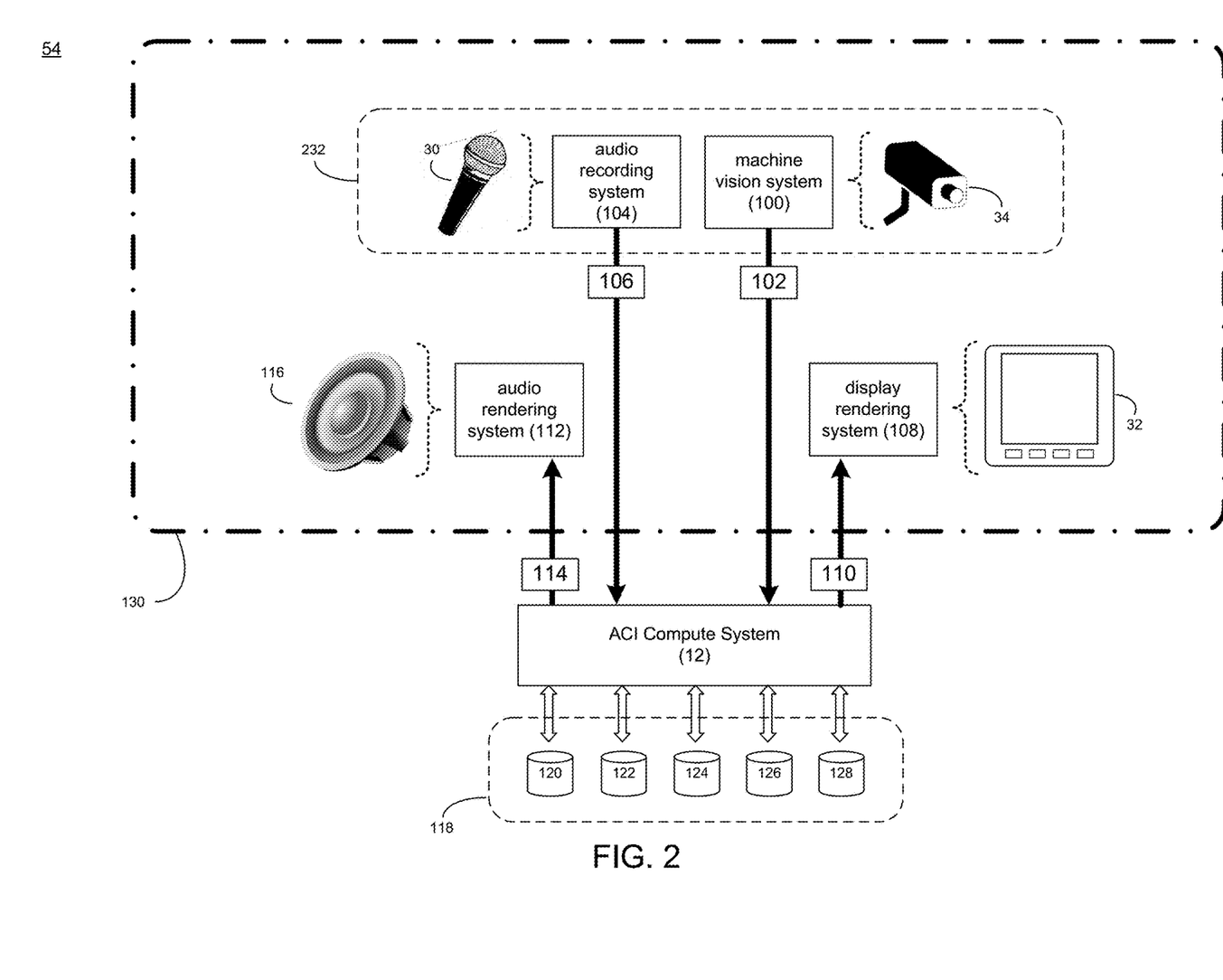
FIG. 2 is a diagrammatic view of a modular ACI system incorporating the automated clinical documentation computer system of FIG. 1.

Referring also to FIG. 2, there is shown a simplified example embodiment of modular ACI system 54 that is configured to automate clinical documentation. Modular ACI system 54 may include: machine vision system 100 configured to obtain machine vision encounter information 102 concerning a patient encounter; audio recording system 104 configured to obtain audio encounter information 106 concerning the patient encounter; and a computer system (e.g., ACI computer system 12) configured to receive machine vision encounter information 102 and audio encounter information 106 from machine vision system 100 and audio recording system 104 (respectively). Modular ACI system 54 may also include: display rendering system 108 configured to render visual information 110; and audio rendering system 112 configured to render audio information 114, wherein ACI computer system 12 may be configured to provide visual information 110 and audio information 114 to display rendering system 108 and audio rendering system 112 (respectively).

Example of machine vision system 100 may include but are not limited to: one or more ACI client electronic devices (e.g., ACI client electronic device 34, examples of which may include but are not limited to an RGB imaging system, an infrared imaging system, a ultraviolet imaging system, a laser imaging system, a SONAR imaging system, a RADAR imaging system, and a thermal imaging system). Examples of audio recording system 104 may include but are not limited to: one or more ACI client electronic devices (e.g., ACI client electronic device 30, examples of which may include but are not limited to a handheld microphone, a lapel microphone, an embedded microphone (such as those embedded within eyeglasses, smart phones, tablet computers and/or watches) and an audio recording device). Examples of display rendering system 108 may include but are not limited to: one or more ACI client electronic devices (e.g., ACI client electronic device 32, examples of which may include but are not limited to a tablet computer, a computer monitor, and a smart television). Examples of audio rendering system 112 may include but are not limited to: one or more ACI client electronic devices (e.g., audio rendering device 116, examples of which may include but are not limited to a speaker system, a headphone system, and an earbud system).

As will be discussed below in greater detail, ACI computer system 12 may be configured to access one or more datasources 118 (e.g., plurality of individual datasources 120, 122, 124, 126, 128), examples of which may include but are not limited to one or more of a user profile datasource, a voice print datasource, a voice characteristics datasource (e.g., for adapting the automated speech recognition models), a face print datasource, a humanoid shape datasource, an utterance identifier datasource, a wearable token identifier datasource, an interaction identifier datasource, a medical conditions symptoms datasource, a prescriptions compatibility datasource, a medical insurance coverage datasource, and a home healthcare datasource. While in this particular example, five different examples of datasources 118, are shown, this is for illustrative purposes only and is not intended to be a limitation of this disclosure, as other configurations are possible and are considered to be within the scope of this disclosure.

As will be discussed below in greater detail, modular ACI system 54 may be configured to monitor a monitored space (e.g., monitored space 130) in a clinical environment, wherein examples of this clinical environment may include but are not limited to: a doctor's office, a medical facility, a medical practice, a medical lab, an urgent care facility, a medical clinic, an emergency room, an operating room, a hospital, a long term care facility, a rehabilitation facility, a nursing home, and a hospice facility. Accordingly, an example of the above-referenced patient encounter may include but is not limited to a patient visiting one or more of the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility).

Machine vision system 100 may include a plurality of discrete machine vision systems when the above-described clinical environment is larger or a higher level of resolution is desired. As discussed above, examples of machine vision system 100 may include but are not limited to: one or more ACI client electronic devices (e.g., ACI client electronic device 34, examples of which may include but are not limited to an RGB imaging system, an infrared imaging system, an ultraviolet imaging system, a laser imaging system, a SONAR imaging system, a RADAR imaging system, and a thermal imaging system). Accordingly, machine vision system 100 may include one or more of each of an RGB imaging system, an infrared imaging systems, an ultraviolet imaging systems, a laser imaging system, a SONAR imaging system, a RADAR imaging system, and a thermal imaging system.

Audio recording system 104 may include a plurality of discrete audio recording systems when the above-described clinical environment is larger or a higher level of resolution is desired. As discussed above, examples of audio recording system 104 may include but are not limited to: one or more ACI client electronic devices (e.g., ACI client electronic device 30, examples of which may include but are not limited to a handheld microphone, a lapel microphone, an embedded microphone (such as those embedded within eyeglasses, smart phones, tablet computers and/or watches) and an audio recording device). Accordingly, audio recording system 104 may include one or more of each of a handheld microphone, a lapel microphone, an embedded microphone (such as those embedded within eyeglasses, smart phones, tablet computers and/or watches) and an audio recording device.

Display rendering system 108 may include a plurality of discrete display rendering systems when the above-described clinical environment is larger or a higher level of resolution is desired. As discussed above, examples of display rendering system 108 may include but are not limited to: one or more ACI client electronic devices (e.g., ACI client electronic device 32, examples of which may include but are not limited to a tablet computer, a computer monitor, and a smart television). Accordingly, display rendering system 108 may include one or more of each of a tablet computer, a computer monitor, and a smart television.

Audio rendering system 112 may include a plurality of discrete audio rendering systems when the above-described clinical environment is larger or a higher level of resolution is desired. As discussed above, examples of audio rendering system 112 may include but are not limited to: one or more ACI client electronic devices (e.g., audio rendering device 116, examples of which may include but are not limited to a speaker system, a headphone system, or an earbud system). Accordingly, audio rendering system 112 may include one or more of each of a speaker system, a headphone system, or an earbud system.

ACI computer system 12 may include a plurality of discrete computer systems. As discussed above, ACI computer system 12 may include various components, examples of which may include but are not limited to: a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform. Accordingly, ACI computer system 12 may include one or more of each of a personal computer, a server computer, a series of server computers, a mini computer, a mainframe computer, one or more Network Attached Storage (NAS) systems, one or more Storage Area Network (SAN) systems, one or more Platform as a Service (PaaS) systems, one or more Infrastructure as a Service (IaaS) systems, one or more Software as a Service (SaaS) systems, a cloud-based computational system, and a cloud-based storage platform.

Figure 3:
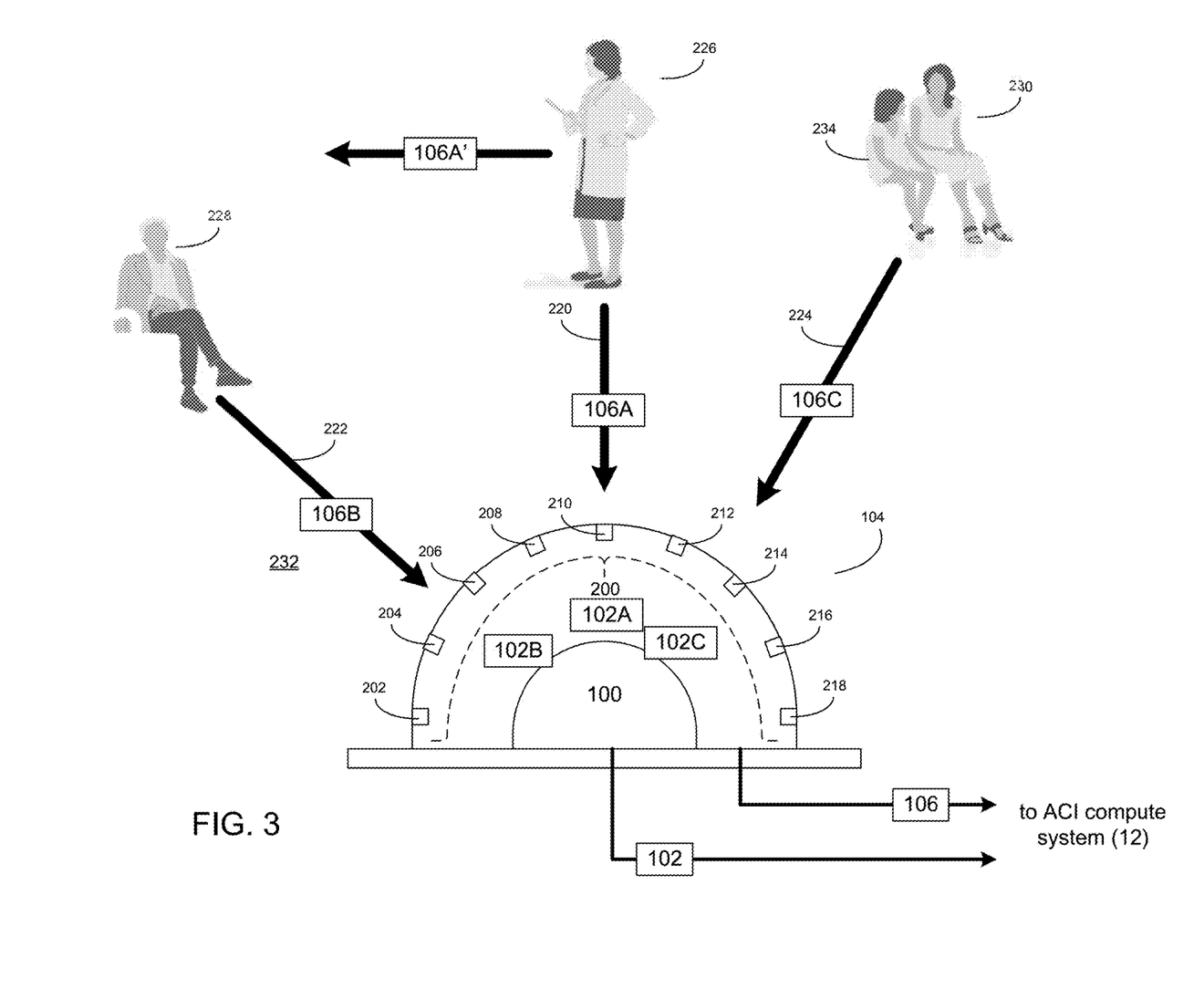
FIG. 3 is a diagrammatic view of a mixed-media ACI device included within the modular ACI system of FIG. 2.

Referring also to FIG. 3, audio recording system 104 may include directional microphone array 200 having a plurality of discrete microphone assemblies. For example, audio recording system 104 may include a plurality of discrete audio acquisition devices (e.g., audio acquisition devices 202, 204, 206, 208, 210, 212, 214, 216, 218) that may form microphone array 200. As will be discussed below in greater detail, modular ACI system 54 may be configured to form one or more audio recording beams (e.g., audio recording beams 220, 222, 224) via the discrete audio acquisition devices (e.g., audio acquisition devices 202, 204, 206, 208, 210, 212, 214, 216, 218) included within audio recording system 104.

For example, modular ACI system 54 may be further configured to steer the one or more audio recording beams (e.g., audio recording beams 220, 222, 224) toward one or more encounter participants (e.g., encounter participants 226, 228, 230) of the above-described patient encounter. Examples of the encounter participants (e.g., encounter participants 226, 228, 230) may include but are not limited to: medical professionals (e.g., doctors, nurses, physician's assistants, lab technicians, physical therapists, scribes (e.g., a transcriptionist) and/or staff members involved in the patient encounter), patients (e.g., people that are visiting the above-described clinical environments for the patient encounter), and third parties (e.g., friends of the patient, relatives of the patient and/or acquaintances of the patient that are involved in the patient encounter).

Accordingly, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam. For example, modular ACI system 54 and/or audio recording system 104 may be configured to utilize audio acquisition device 210 to form audio recording beam 220, thus enabling the capturing of audio (e.g., speech) produced by encounter participant 226 (as audio acquisition device 210 is pointed to (i.e., directed toward) encounter participant 226). Additionally, modular ACI system 54 and/or audio recording system 104 may be configured to utilize audio acquisition devices 204, 206 to form audio recording beam 222, thus enabling the capturing of audio (e.g., speech) produced by encounter participant 228 (as audio acquisition devices 204, 206 are pointed to (i.e., directed toward) encounter participant 228). Additionally, modular ACI system 54 and/or audio recording system 104 may be configured to utilize audio acquisition devices 212, 214 to form audio recording beam 224, thus enabling the capturing of audio (e.g., speech) produced by encounter participant 230 (as audio acquisition devices 212, 214 are pointed to (i.e., directed toward) encounter participant 230). Further, modular ACI system 54 and/or audio recording system 104 may be configured to utilize null-steering precoding to cancel interference between speakers and/or noise.

As is known in the art, null-steering precoding is a method of spatial signal processing by which a multiple antenna transmitter may null multiuser interference signals in wireless communications, wherein null-steering precoding may mitigate the impact off background noise and unknown user interference.

In particular, null-steering precoding may be a method of beamforming for narrowband signals that may compensate for delays of receiving signals from a specific source at different elements of an antenna array. In general and to improve performance of the antenna array, in incoming signals may be summed and averaged, wherein certain signals may be weighted and compensation may be made for signal delays.

Machine vision system 100 and audio recording system 104 may be stand-alone devices (as shown in FIG. 2). Additionally/alternatively, machine vision system 100 and audio recording system 104 may be combined into one package to form mixed-media ACI device 232. For example, mixed-media ACI device 232 may be configured to be mounted to a structure (e.g., a wall, a ceiling, a beam, a column) within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility), thus allowing for easy installation of the same. Further, modular ACI system 54 may be configured to include a plurality of mixed-media ACI devices (e.g., mixed-media ACI device 232) when the above-described clinical environment is larger or a higher level of resolution is desired.

Modular ACI system 54 may be further configured to steer the one or more audio recording beams (e.g., audio recording beams 220, 222, 224) toward one or more encounter participants (e.g., encounter participants 226, 228, 230) of the patient encounter based, at least in part, upon machine vision encounter information 102. As discussed above, mixed-media ACI device 232 (and machine vision system 100/audio recording system 104 included therein) may be configured to monitor one or more encounter participants (e.g., encounter participants 226, 228, 230) of a patient encounter.

Specifically, machine vision system 100 (either as a stand-alone system or as a component of mixed-media ACI device 232) may be configured to detect humanoid shapes within the above-described clinical environments (e.g., a doctor's office, a medical facility, a medical practice, a medical lab, an urgent care facility, a medical clinic, an emergency room, an operating room, a hospital, a long term care facility, a rehabilitation facility, a nursing home, and a hospice facility). And when these humanoid shapes are detected by machine vision system 100, modular ACI system 54 and/or audio recording system 104 may be configured to utilize one or more of the discrete audio acquisition devices (e.g., audio acquisition devices 202, 204, 206, 208, 210, 212, 214, 216, 218) to form an audio recording beam (e.g., audio recording beams 220, 222, 224) that is directed toward each of the detected humanoid shapes (e.g., encounter participants 226, 228, 230).

As discussed above, ACI computer system 12 may be configured to receive machine vision encounter information 102 and audio encounter information 106 from machine vision system 100 and audio recording system 104 (respectively); and may be configured to provide visual information 110 and audio information 114 to display rendering system 108 and audio rendering system 112 (respectively). Depending upon the manner in which modular ACI system 54 (and/or mixed-media ACI device 232) is configured, ACI computer system 12 may be included within mixed-media ACI device 232 or external to mixed-media ACI device 232.

As discussed above, ACI computer system 12 may execute all or a portion of secure training process 10, wherein the instruction sets and subroutines of secure training process 10 (which may be stored on one or more of e.g., storage devices 16, 20, 22, 24, 26) may be executed by ACI computer system 12 and/or one or more of ACI client electronic devices 28, 30, 32, 34.

The Secure Training Process:

As discussed above, processing and storing audio encounter information and corresponding transcriptions for training a speech processing system or model present a security concern. For example, sensitive content may be obtained by a breach. For example, an internal actor could potentially scan lots of internal data (e.g., by looking for particular persons or classes of information, such as credit card numbers). However, just removing or obscuring sensitive content may result in degraded speech processing system performance. For example and as discussed above, conventional approaches that seek to obscure audio encounter information and corresponding textual data using text-to-speech systems result in less accurate speech processing (i.e., increased word error rate in machine-based speech processing).

Figure 4:
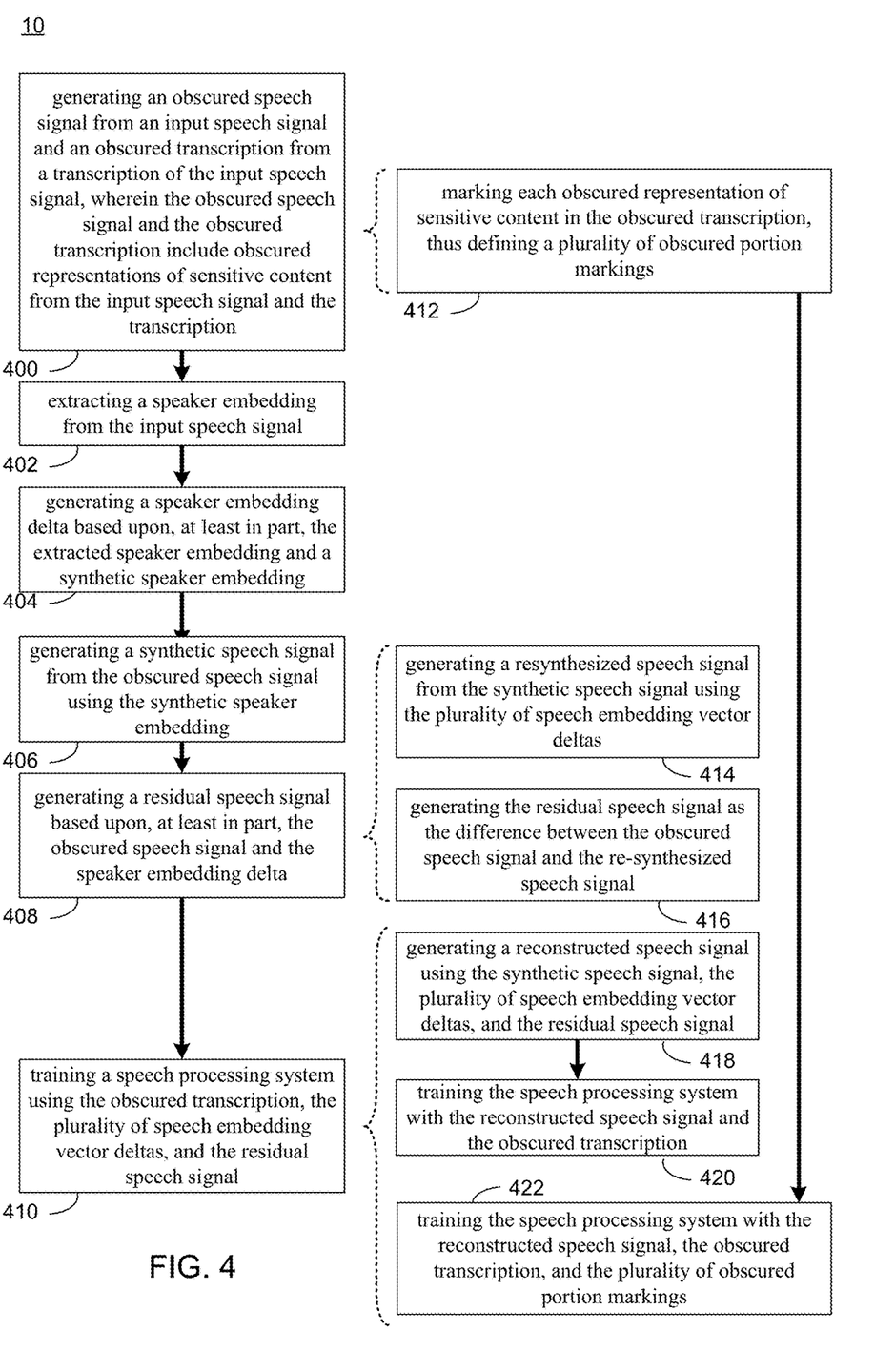
FIG. 4 is a flow chart of one implementation of the secure training process of FIG. 1.
Figure 5:
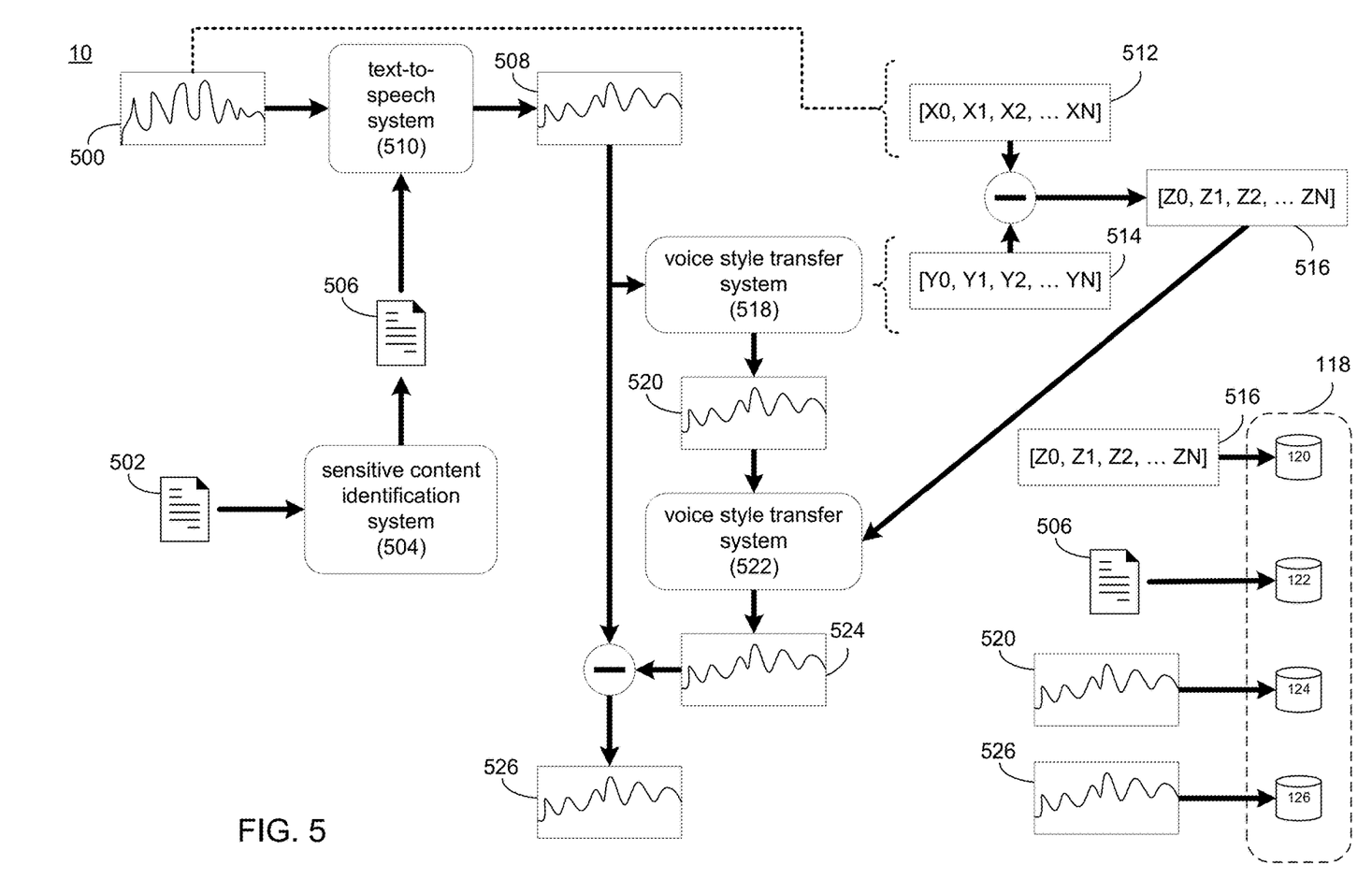
FIGS. 5-6 are diagrammatic views of the secure training process of FIG. 1.
Figure 6:
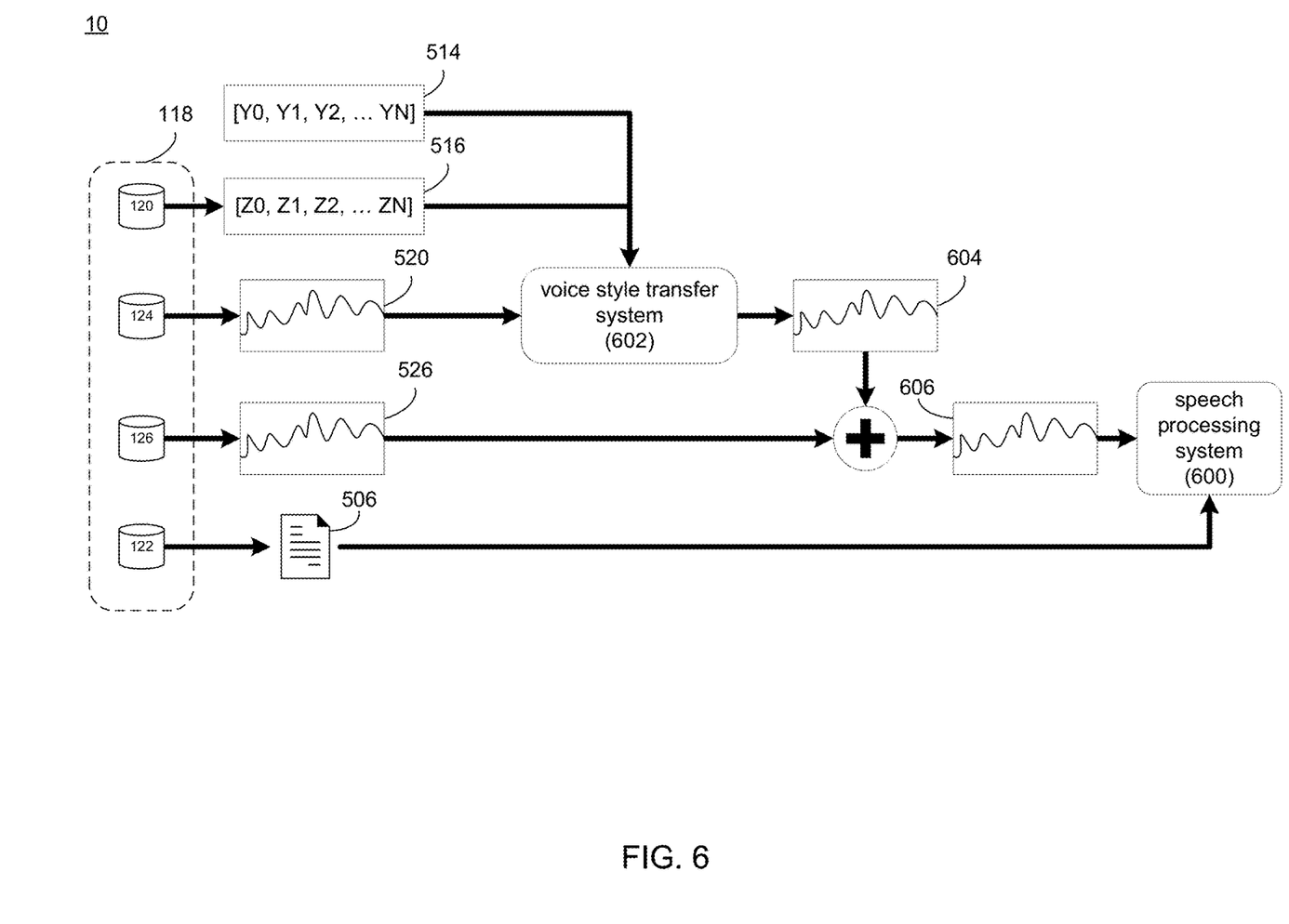

Referring also at least to FIGS. 4-6, secure training process 10 may generate 400 an obscured speech signal from an input speech signal and an obscured transcription from a transcription of the input speech signal, where the obscured speech signal and the obscured transcription include obscured representations of sensitive content from the input speech signal and the transcription. A speaker embedding may be extracted 402 from the input speech signal. A speaker embedding delta may be generated 404 based upon, at least in part, the extracted speaker embedding and a synthetic speaker embedding. A synthetic speech signal may be generated 406 from the obscured speech signal using the synthetic speaker embedding. A residual signal may be generated 408 based upon, at least in part, the obscured speech signal and the speaker embedding delta. A speech processing system may be trained 410 using the obscured transcription, the synthetic speech signal, the speaker embedding delta, and the residual signal.

As will be discussed in greater below, secure training process 10 may receive an input speech signal (i.e., a portion of audio information) and a transcription of the input speech signal to generate an obscured transcription (i.e., a version of the transcription in which sensitive content is replaced with surrogate data) and an obscured speech signal (i.e., a version of the input speech signal that is fully intelligible but with the audio portions of the sensitive content replaced with surrogate data). A speaker embedding delta (i.e., a representation of the difference or delta between the original speaker's voice style and a synthetic speaker's voice style) may be generated. A synthetic speech signal (i.e., a version of the obscured speech signal with the voice style changed to sound like another speaker) may be generated from the obscured speech signal. The obscured speech signal and the synthetic speech signal may be used to generate a residual signal (i.e., audio information capturing the difference between the synthetic speech signal and the obscured speech signal that accounts for non-speech acoustic properties present in the obscured speech signal (e.g., noise, reverberation, etc.) that are filtered from the synthetic speech signal). The synthetic speech signal, the obscured transcription, the speaker embedding delta, and the residual speech signal may be used to generate a reconstructed speech signal (i.e., a representation of the input speech signal without the sensitive content while including the acoustic properties of the obscured speech signal) for training a speech processing system.

In some implementations, secure training process 10 may receive an input speech signal. For example and as discussed above, an audio recording system (e.g., audio recording system 104) may receive and record an input speech signal. Referring also to FIG. 5, secure training process 10 may receive an input speech signal (e.g., input speech signal 500). In one example, input speech signal 500 may be received and recorded by an audio recording system (e.g., audio recording system 104) and/or may be a previously recorded audio input signal (e.g., an audio signal stored in a database or other data structure). In one example, suppose that input speech signal 500 concerns a medical encounter between a medical professional (e.g., participant 226) and a patient (e.g., participant 228). In this example, the patient (e.g., participant 228) may be asked by the medical professional (e.g., participant 226) to audibly confirm personal identification information (e.g., name, date of birth, marital status, etc.) during a medical examination. Additionally, the patient (e.g., participant 228) may describe personal health information (e.g., symptoms, medical history, etc.). Accordingly, input speech signal 500 may include sensitive content.

In some implementations, secure training process 10 may receive a transcription of the input speech signal. For example, secure training process 10 may provide the input speech signal (e.g., input speech signal 500) to an automatic speech recognition (ASR) system or other speech processing system to generate a transcription (e.g., transcription 502) of the input speech signal (e.g., input speech signal 500). As is known in the art, ASR systems may convert input speech signals to output text. Accordingly, the ASR system may automatically generate transcription 502 of input speech signal 500. As will be discussed in greater detail below, transcription 502 may include any sensitive content information recorded in input speech signal 500.

In some implementations, secure training process 10 may identify one or more sensitive content portions from the transcription of the input speech signal. Sensitive content portions may generally include any pieces or types of information that are personal, private, or subject to confidentiality. For example, the one or more sensitive content portions may include personally identifiable information (PII) and/or protected health information (PHI). In addition to PII and PHI, sensitive content portions may include financial information, intellectual property, trade secrets, and/or information declared private by law or regulation. Accordingly, it will be appreciated that secure training process 10 may identify various types of information as sensitive content within the scope of the present disclosure.

For example, secure training process 10 may utilize a sensitive content identification system (e.g., sensitive content identification system 504) to identify one or more sensitive content portions within the transcription (e.g., transcription 502). Sensitive content identification system 504 may include various known components such as natural language understanding (NLU) systems, artificial intelligence/machine learning models, predefined detection rules, etc. for identifying one or more sensitive content portions from within the transcription. Secure training process 10 may provide a user interface, database, and/or other data structure of examples and/or rules for identifying sensitive content within a transcription.

In some implementations, secure training process 10 may generate 400 an obscured speech signal from an input speech signal and an obscured transcription from a transcription of the input speech signal, where the obscured speech signal and the obscured transcription include obscured representations of sensitive content from the input speech signal and the transcription. In this manner, the obscured speech signal is fully intelligible but with sensitive content (i.e., PHI/PII) replaced with surrogate data. Generating 400 the obscured transcription may generally include "obscuring" the one or more sensitive content portions from the transcription. For example, secure training process 10 may obscure the sensitive content by replacing and/or modifying the sensitive content portions from the transcription. For example, secure training process 10 may utilize various known components such as natural language understanding (NLU) systems, artificial intelligence/machine learning models, predefined detection rules, etc. for obscuring (i.e., substituting) particular portions of sensitive content. Obscuring the one or more sensitive content portions from the transcription may include changing personally identifiable information (PII) and/or protected health information (PHI). For example, secure training process 10 may include rules for replacing particular types of sensitive content with similar types of content. In this manner, secure training process 10 may obscure sensitive content particular to individuals associated with a particular input speech signal.

In some implementations, secure training process 10 may generate 400 the obscured transcription and the obscured speech signal by processing the transcription and corresponding portions of the input speech signal in segments. For example, secure training process 10 may process each segment of input speech signal 500 and transcription 502 associated with a particular speaker. For example, secure training process 10 may utilize a speaker identification system (e.g., a speaker recognition system) to identify particular speakers in an input speech signal. As will be discussed in greater detail below, acoustic properties of a speaker's voice may be represented as a speaker embedding. Secure training process 10 may identify one or more speakers from input speech signal 500 by extracting speaker embeddings for distinct speakers.

Additionally, transcription 502 may include predefined speaker tags indicating conversational data (i.e., text) that is attributable to a particular speaker (e.g., during an encounter between various encounter participants as shown in FIG. 3). In this manner, secure training process 10 may generate 400 the obscured transcription by processing segments of text of the transcription. For example, a segment may be a predefined amount of text and/or amount of corresponding speech signal. In another example, a segment may represent a portion of text and/or corresponding speech signal associated with a particular speaker. In this example, a first segment may include a portion of the transcription associated with a particular speaker while a second segment may include another portion of the transcription that is associated with another speaker. In some implementations, a segment may be defined as a sensitive content portion. For example, in response to identifying sensitive content within the transcription, secure training process 10 may define a segment for each sensitive content portion. While various examples have been described about how a segment may be defined, it will be appreciated that the segment may be given by a single speaker and may include any fixed or dynamic length or amount of content from the transcription and/or the input speech signal within the scope of the present disclosure.

Suppose that secure training process 10 identifies various sensitive content portions from transcription 502. In this example, suppose secure training process 10 identifies the doctor's name (e.g., "James"). In this example, secure training process 10 may obscure the doctor's name (e.g., replacing "James" with "Andy"). Similarly, secure training process 10 may obscure e.g., a patient's date of birth (e.g., replacing "Oct. 12, 1987" with "Nov. 12, 1997"); and/or other various sensitive content (e.g., a patient's medical history/prescription dosage information, an individual's financial information, a participant's address, etc.). Secure training process 10 may output these obscured sensitive data portions in the form of an obscured transcription (e.g., obscured transcription 506). In some implementations, for non-sensitive content portions, secure training process 10 may utilize the text of the transcription without performing any modifications. For sensitive content, secure training process 10 may obscure those sensitive content portions by replacing or modifying the original text of the transcription. In this manner, secure training process 10 may generate obscured transcription 506 by processing each segment of original transcription 502 individually for sensitive content. While several examples of obscuring sensitive content portions has been described above, it will be appreciated that any combination of sensitive content portions may be obscured by secure training process 10 within the scope of the present disclosure.

Secure training process 10 may generate 400 an obscured speech signal with speech content for modified portions of the obscured transcription relative to the original transcription. For example, an obscured speech signal (e.g., obscured speech signal 508) may be generated using a text-to-speech (TTS) system (e.g., TTS system 510) configured to convert obscured representations of the obscured transcription (e.g., transcription 506) into an obscured speech signal (e.g., obscured speech signal 508). TTS system 510 may include any TTS system known in the art. As discussed above, secure training process 10 may generate an obscured speech signal corresponding to particular segments of the obscured transcription. For example, secure training process may use TTS system 510 to replace the speech signal portions including sensitive content with a synthesized representation of the sensitive content portions.

For example, secure training process 10 may identify a class for each sensitive content portion (e.g., age, gender, date, time, location, etc.). Secure training process 10 may replace the sensitive content portion with a class identifier or tag. For example, if transcription 502 states "Sam has an appointment", secure training process 10 may identify "Sam" as PII and as PHI. In this example, secure training process 10 may access one or more datasources (e.g., datasources 118) to identify the class or classes for each sensitive content portion in the transcription and the input speech signal. In response to identifying and replacing each sensitive content portion with a corresponding class identifier, secure training process 10 may access a dictionary or other database of candidate phrases to use as a replacement for the class identifier. Secure training process 10 may replace each class identifier with one or more candidate phrases from the database of candidate phrases.

Continuing with the above example, suppose that obscured transcription 506 includes an obscured representation of the doctor's name (e.g., "James" is replaced with "Andy") and an obscured representation of the patient's date of birth (e.g., "Oct. 12, 1987" is replaced with "Nov. 12, 1997"). In this example, secure training process 10 may use TTS system 510 to generate obscured speech representations of "Andy" and "Oct. 12, 1987". While an example with two obscured portions has been described, it will be appreciated that this is for example purposes only and that any number of obscured representations may be processed by TTS system 510 within the scope of the present disclosure.

In some implementations, secure training process 10 may mark 412 each obscured representation of sensitive content in the obscured transcription, thus defining a plurality of obscured portion markings. For example, secure training process 10 may generate a marker or other tag for each obscured representation of sensitive content in the obscured transcription. In one example, secure training process 10 may provide a marker for each portion or segment of the obscured transcription to identify obscured portions. For example, a "0" may indicate that the segment is not obscured while a "1" may indicate that the segment is obscured. While an example of a single value indicator has been provided, it will be appreciated that a list or table of obscured portions may be defined for the obscured transcription. As such, secure training process 10 may mark 412 each observed representation of sensitive content in various ways and at various granularities (e.g., per segment, per line of the transcription, per frame of the input speech signal, etc.) within the scope of the present disclosure.

As will be discussed in greater detail below, secure training process 10 may utilize the plurality of obscured portion markings to indicate where, in the corresponding speech signal, a portion of the original input speech signal has been obscured. In some implementations, the plurality of obscured portion markings may be utilized during the training of a speech processing system to inform the speech processing system of obscured speech signal portions. For example, TTS system 510 may process each obscured representation of sensitive content to generate a synthetic, obscured representation of the sensitive content. However, these obscured representations may be anechoic (i.e., lacking any noise, reverberation, or other acoustic properties). As such, when used in training, the obscured representations may not be representative of the various acoustic properties of the actual input speech signal (i.e., noise level, reverberation, etc.). Accordingly, simply using the obscured representations from the obscured speech signal for training may result in degraded speech processing system performance (e.g., higher word error rate and other performance degradations). In this manner, secure training process 10 may use the plurality of obscured portion markings to inform the speech processing system which portions of the obscured speech signal are representative of actual input speech during training.

In some implementations, secure training process 10 may extract 402 a speaker embedding from the input speech signal. As is known in the art, a speaker embedding may generally include a representation a speaker's identity (e.g., a vector of fixed size) regardless of the length of an input speech signal. A speaker embedding may be generated in various ways within the scope of the present disclosure. For example and as known in the art, secure training process 10 may perform feature extraction by building a supervised deep neural network (DNN), operating at the frame level, to classify speakers in a development set. The input of this background network may be formed by stacking each training frame with its left and right context frames. The number of outputs corresponds to the number of speakers in the development set, N. The target labels may be formed as a 1-hot N-dimensional vector where the only non-zero component is the one corresponding to the speaker identity. Once the DNN has been trained successfully, the accumulated output activations of the last hidden layer may be used as a new speaker representation or speaker embedding. That is, for every frame of the obscured speech signal belonging to a new speaker, the output activations of the last hidden layer may be computed using standard feedforward propagation in the trained DNN, and then those activations may be accumulated to form a new compact representation of that speaker, the speaker embedding. In this example, the speaker embedding may be referred to as a "d-vector". However, it will be appreciated that various types of speaker embeddings may be extracted from the obscured speech signal within the scope of the present disclosure.

Referring again to the example of FIG. 5, secure training process 10 may extract 402, for each segment of the input speech signal (e.g., input speech signal 500) and for each speaker (e.g., participant 226 and/or participant 228), a speaker embedding (e.g., speaker embedding 512). In some implementations, speaker embedding 512 may be a d-vector that represents the average activations from a last hidden layer of a DNN. In this manner, secure training process 10 may utilize speaker embedding 512 to represent the speech characteristics of a particular participant (e.g., participant 226 or participant 228).

In some implementations, secure training process 10 may generate 404 a speaker embedding delta based upon, at least in part, the extracted speaker embedding and a synthetic speaker embedding. A synthetic speaker embedding may represent the speech characteristics of another person or an artificially created speaker embedding that is useable for generating and storing speech signals. For example, a speaker embedding (e.g., speaker embedding 512) may be directly or indirectly attributable to a particular person and, as such, may constitute sensitive content (i.e., PII). In this example, a synthetic speaker embedding (e.g., synthetic speaker embedding 514) may represent a licensed or otherwise useable speaker embedding that may be used for generating synthetic speech signals without comprising PII. As such, the term "synthetic" may represent any speaker embedding that does not constitute sensitive content (i.e., PII that is attributable to a known person but used without their consent). For example, various laws and regulations limit the amount of PII or PHI that can be stored or utilized in speech processing. As such, synthetic speaker embedding 514 may represent a legally compliant speaker embedding that can be used to generate synthetic speech signals.

In some implementations, secure training process 10 may select synthetic speaker embedding 514 by comparing extracted speaker embedding 512 to a plurality of candidate synthetic speaker embeddings. For example, secure training process 10 may ensure that the synthetic speaker embedding is sufficiently different from the original speaker embedding. In one example, secure training process 10 may determine the distance between the extracted speaker embedding and each synthetic speaker embedding and may select a synthetic speaker embedding based upon a predefined threshold. For example, a threshold may be defined such that the difference between the extracted speaker embedding and the selected synthetic speaker embedding is greater than or equal to the threshold. While one example has been described for selecting a synthetic speaker embedding, it will be appreciated various methodologies may be used to select the synthetic speaker embedding within the scope of the present disclosure.

In some implementations, a speaker embedding delta may represent the difference between an extracted speaker embedding (e.g., speaker embedding 512) and a synthetic speaker embedding (e.g., synthetic speaker embedding 514). For example, extracted speaker embedding 512 may include PII that is attributable to a particular speaker. As such, storing extracted speaker embedding 512 may represent a security risk. Accordingly, secure training process 10 may generate 404 a speaker embedding delta (e.g., speaker embedding delta 516) as the distance or difference between extracted speaker embedding 512 and synthetic speaker embedding 514. In this manner, by generating speaker embedding delta 516, a speaker embedding for a particular speaker may be securely derivable without actually storing sensitive content (i.e., PII).

In one example, speaker embedding delta 516 may be the Euclidean distance between speaker embedding 512 and synthetic speaker embedding 514. Specifically, speaker embedding delta 516 may be generated as a d-vector delta between the extracted speaker d-vector and the synthetic d-vector. While one example of how speaker embedding delta 516 has been discussed, it will be appreciated that this is for example purposes only and that various approaches may be used to determine the distance or difference between the synthetic speaker embedding and the extracted speaker embedding within the scope of the present disclosure. In some implementations and as discussed above, secure training process 10 may generate 404 a speaker embedding delta for each segment of the obscured speech signal. As will be discussed in greater detail below, secure training process 10 may generate speaker embedding delta 516 as a mapping between extracted speaker embedding 512 and synthetic speaker embedding 514 to allow for the reconstruction of the input speech signal with the extracted speaker embedding to train a speech processing system without storing or otherwise retaining the extracted speaker embedding 512 or other sensitive content.

In some implementations, secure training process 10 may generate 406 a synthetic speech signal from the obscured speech signal using the synthetic speaker embedding. A synthetic speech signal may include a representation of the obscured speech signal generated with a voice style transfer system or other speech-to-speech system. For example and as discussed above, obscured speech signal 508 may include obscured representations of sensitive content generated using TTS system 510. However, obscured speech signal 508 may include non-sensitive portions from input speech signal 500 and obscured portions from TTS system 510. As such, obscured speech signal 508 may not be consistent or representative of the actual speech signal sent to a speech processing system. Accordingly, secure training process 10 may utilize a voice style transfer (VST) system (e.g., VST system 518) to generate a complete synthetic speech signal (e.g., synthetic speech signal 520).

Generating 406 the synthetic speech signal from the obscured speech signal may include processing the obscured speech signal using a VST system with a synthetic speaker embedding. For example and as is known in the art, a VST system synthesizes speech from one source speaker to a different target speaker while keeping the linguistic information while transferring the speech style to the target speaker. Secure training process 10 may utilize various known VST systems (e.g., neural networks, generative adversarial networks (GANs), etc.) for VST system 518. VST system 518 may generate 406 synthetic speech signal 520 using synthetic speaker embedding 514. For example, VST system 518 may utilize synthetic speaker embedding 514 to modify the various acoustic properties or features of obscured speech signal 508 to generate synthetic speech signal 520 that has the speech characteristics of synthetic speaker embedding 514. In this manner, synthetic speech signal 520 may sound as if it were spoken by the same speaker associated with synthetic speaker embedding 514. As such, synthetic speech signal 520 may represent a secure version of input speech signal 500 without any sensitive content (e.g., PII or PHI).

In some implementations, secure training process 10 may generate 408 a residual signal based upon, at least in part, the obscured speech signal and the speaker embedding delta. As discussed above, synthetic speech signal 520 may represent a secure version of input speech signal 500 that does not contain sensitive content (e.g., PII or PHI). However, as synthetic speech signal 520 is synthetically generated, it does not match the actual input speech signal (e.g., input speech signal 500) and, as such, does not represent what a speech processing system receives in normal use (e.g., as synthetic speech signal is anechoic). If the speech processing system is trained using synthetic speech signal 520, the speech processing system may not account for the acoustic properties of the actual input speech that is normally received by the audio recording system (e.g., audio recording system 104). As such, the performance of the speech processing system may be degraded if training is performed using synthetic speech signal 520. Accordingly, secure training process 10 may generate 408 a residual signal that accounts for the acoustic properties that are modified or removed when generating synthetic speech signal 520. As will be discussed in greater detail below, secure training process 10 may utilize the residual signal to reconstruct the input speech signal, including various acoustic properties (e.g., noise, reverberation, etc.) when training the speech processing system without storing or otherwise retaining sensitive content.

In some implementations, generating 408 a residual signal based upon, at least in part, the obscured speech signal and the speaker embedding delta may include generating 416 a resynthesized speech signal from the synthetic speech signal using the speaker embedding delta. For example, secure training process 10 may utilize a VST system (e.g., VST system 522) and the speaker embedding delta (e.g., speaker embedding delta 516) to generate a "resynthesized" speech signal that includes the speech characteristics defined by the speaker embedding delta (e.g., resynthesized speech signal 524). While VST system 522 is shown in addition to VST system 518, it will be appreciated that any number of VST systems may be used within the scope of the present disclosure. For example, VST systems 518 and 522 may be the same VST system used with different inputs at different times or may represent separate VST systems. In some implementations, resynthesized speech signal 524 may map back to the extracted speaker embedding (e.g., speaker embedding 512) without storing or otherwise retaining the extracted speaker embedding. In this manner, secure training process 10 may securely generate 414 a resynthesized representation of the obscured speech signal without storing sensitive content in the form of speaker embeddings extracted from the input speech signal.

In some implementations, generating 408 a residual signal based upon, at least in part, the obscured speech signal and the speaker embedding delta may include generating 416 the residual signal as the difference between the obscured speech signal and the resynthesized speech signal. In this manner, residual signal 526 may include any speaker and background acoustic information from the obscured speech signal (e.g., obscured speech signal 508) that is missing or corrupted in the resynthesized speech signal (e.g., resynthesized speech signal 524). As shown in FIG. 5, residual signal 526 may be generated 416 by determining the difference between obscured speech signal 508 and resynthesized speech signal 524. In some implementations, residual signal 526 may be generated 408 in the feature domain or in a neural embedding domain (i.e., after a first encoder layer). This may result in a more secure residual signal than a waveform difference. However, it will be appreciated that residual signal 526 may be generated 416 from resynthesized speech signal 524 and obscured speech signal 508 in various ways within the scope of the present disclosure.

In some implementations, secure training process 10 may securely store the obscured transcription, the speaker embedding delta, the synthetic speech signal, and the residual signal. For example and as shown in FIG. 5, secure training process 10 may store obscured transcription 506, speaker embedding delta 516, synthetic speech signal 520, and residual signal 526 in one or more storage devices or datasources (e.g., datasource 118). In one example, secure training process 10 may store speaker embedding delta 516 in one datasource (e.g., datasource 120); obscured transcription 506 in another datasource (e.g., datasource 122); synthetic speech signal 520 in another datasource (e.g., datasource 124); and residual signal 526 in another datasource (e.g., datasource 126). In this manner, secure training process 10 may securely store obscured transcription 506, speaker embedding delta 516, synthetic speech signal 520, and residual signal 526 in various datasources to reduce the likelihood of a breach revealing any singular representation of sensitive content. For example, without each of obscured transcription 506, speaker embedding delta 516, synthetic speech signal 520, and residual signal 526, reconstruction of input speech signal 500 may not be possible. While an example is shown with each of obscured transcription 506, speaker embedding delta 516, synthetic speech signal 520, and residual signal 526 being stored in separate datasources, it will be appreciated that this is for example purposes only.

For example, obscured transcription 506, speaker embedding delta 516, synthetic speech signal 520, and residual signal 526 may be stored together or apart in any combination across any number of datasources or other storage devices within the scope of the present disclosure. It will also be appreciated that while each of datasources 120, 122, 124, and 126 are shown in a grouping, secure training process 10 may store obscured transcription 506, speaker embedding delta 516, synthetic speech signal 520, and residual signal 526 in any storage device or combination of storage devices locally at and/or remotely from ACI compute system 12 within the scope of the present disclosure.

In some implementations, storing obscured transcription 506, speaker embedding delta 516, synthetic speech signal 520, and residual signal 526 may include encrypting any or all of obscured transcription 506, speaker embedding delta 516, synthetic speech signal 520, and residual signal 526. For example, any known encryption processes may be used to encrypt obscured transcription 506, speaker embedding delta 516, synthetic speech signal 520, and residual signal 526 for storage within the scope of the present disclosure. In response to storing obscured transcription 506, speaker embedding delta 516, synthetic speech signal 520, and residual signal 526, secure training process 10 may discard input speech signal 500, transcription 502, extracted speaker embedding 512, obscured speech signal 508, and resynthesized speech signal 524.

In some implementations, secure training process 10 may train 410 a speech processing system using the obscured transcription, the synthetic speech signal, the speaker embedding delta, and the residual signal. Referring also to FIG. 6, training 410 a speech processing system (e.g., speech processing system 600) may include providing labeled data (e.g., from a transcription) and input speech data for the speech processing system to "learn" from. For example and as is known in the art, machine learning generally includes the training of an algorithm or combination of to recognize certain types of patterns. Machine learning approaches may be generally divided into three categories, depending on the nature of the signal available: supervised learning, unsupervised learning, and reinforcement learning. As is known in the art, supervised learning may include presenting a computing device with example inputs and their desired outputs, given by a "teacher", where the goal is to learn a general rule that maps inputs to outputs. With unsupervised learning, no labels are given to the learning algorithm, leaving it on its own to find structure in its input. Unsupervised learning can be a goal in itself (discovering hidden patterns in data) or a means towards an end (feature learning). As is known in the art, reinforcement learning may generally include a computing device interacting in a dynamic environment in which it must perform a certain goal (such as driving a vehicle or playing a game against an opponent). As it navigates its problem space, the program is provided feedback that's analogous to rewards, which it tries to maximize. While three examples of machine learning approaches have been provided, it will be appreciated that other machine learning approaches are possible within the scope of the present disclosure.

In some implementations, training 410 a speech processing system using the obscured transcription, the synthetic speech signal, the speaker embedding delta, and the residual signal may include generating 418 a reconstructed speech signal using the synthetic speech signal, the speaker embedding delta, and the residual signal. For example and as shown in FIG. 6, suppose a user desires to train speech processing system 600. In this example, the user may select or otherwise indicate training data to use in the training of speech processing system 600. Secure training process 10 may provide various user interfaces to receive the selection of particular training data (e.g., the obscured transcription, the synthetic speech signal, the speaker embedding delta, and the residual signal) for training a speech processing system. In some implementations, each portion of the training data may be associated with each other such that selection of one portion of the training data references each of the other portions of the training data.

In this example, suppose that obscured transcription 506, speaker embedding delta 516, synthetic speech signal 520, and residual signal 526 are selected for training speech processing system 600. Secure training process 10 may obtain obscured transcription 506, speaker embedding delta 516, synthetic speech signal 520, and residual signal 526 from storage (e.g., one or more datasources 118). In this example, secure training process 10 may utilize a VST system (e.g., VST system 602) to generate 418 reconstructed speech signal 606 by processing synthetic speaker embedding 514, speaker embedding delta 516, and synthetic speech signal 520. VST system 602 may generate speech signal 604 that does not include the acoustic properties of residual signal 526. As such, secure training process 10 may generate 418 reconstructed speech signal 606 by combining speech signal 604 generated by VST system 602 with residual signal 526. In this manner, reconstructed speech signal 606 may represent an approximate reconstruction of input speech signal 500.

In some implementations, training 410 a speech processing system using the obscured transcription, the synthetic speech signal, the speaker embedding delta, and the residual signal may include training 420 the speech processing system with the reconstructed speech signal and the obscured transcription. For example, secure training process 10 may provide obscured transcription 506 and reconstructed speech signal 606 to speech processing system 600 as training data. As reconstructed speech signal 606 and obscured transcription 506 are processed to remove sensitive content (e.g., by obscuring PHI and PII in obscured transcription 506) and to approximate the speech characteristics of the previously extracted speaker embedding, speech processing system 600 may be trained 420 to enhance speech processing performance in light of the speech characteristics of reconstructed speech signal 606 and/or the content of obscured transcription 506 without storing sensitive content.

In some implementations, training 410 a speech processing system using the obscured transcription, the synthetic speech signal, the speaker embedding delta, and the residual signal may include training 422 the speech processing system with the reconstructed speech signal, the obscured transcription, and the plurality of obscured portion markings. As discussed above, secure training process 10 may mark 412 each obscured representation of sensitive content in the obscured transcription, thus defining a plurality of obscured portion markings. For example, when obscuring sensitive content, secure training process 10 may generate an obscured speech signal that is anechoic because of the TTS system. As such, these obscured portions of the speech signal may not correspond to what is received and processed by speech processing system 600.

Secure training process 10 may identify, for each segment of the obscured transcription and reconstructed speech signal, whether the segment includes obscured data. For example, if the segment includes a marking (e.g., "1"), the marking may be provided to speech processing system 600 as a label. In this manner, secure training process 10 may train 422 speech processing system 600 to recognize and bias obscured portions differently from non-obscured portions (e.g., as non-obscured portions include the acoustic properties of the input speech signal while obscured portions are generally anechoic). In this manner, secure training process 10 may securely train 410 speech processing system 600 with representative training data without storing sensitive content. Accordingly, secure training process 10 may allow speech processing systems to be trained with training data generated from actual input speech signals without storing sensitive content.

In some implementations and as discussed above, secure training process 10 may train 410 speech processing system 600 segment by segment such that reconstructed speech signal 606 is generated on a segment-by-segment basis. In response to providing each reconstructed segment to speech processing system 600, secure training process 10 may discard the reconstructed segment. In this manner, any potentially sensitive content in each segment of reconstructed speech signal 606 is used only for training and discarded following the training using that segment. For example, during the training of speech processing system 600, the reconstructed signal or segment is never written to disk or other long term memory. Rather, each segment is reconstructed to train speech processing system 600 and then discarded. As such, the reconstructed segment only exists in short term memory for a minimal duration, thus minimizing the risk of a leak or breach during the training process itself.

General:

As will be appreciated by one skilled in the art, the present disclosure may be embodied as a method, a system, or a computer program product. Accordingly, the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present disclosure may take the form of a computer program product on a computer-usable storage medium having computer-usable program code embodied in the medium.

Any suitable computer usable or computer readable medium may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium may include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device. The computer-usable or computer-readable medium may also be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, communicate, propagate, or transport the program for use by or in connection with the instruction execution system, apparatus, or device. The computer-usable medium may include a propagated data signal with the computer-usable program code embodied therewith, either in baseband or as part of a carrier wave. The computer usable program code may be transmitted using any appropriate medium, including but not limited to the Internet, wireline, optical fiber cable, RF, etc.

Computer program code for carrying out operations of the present disclosure may be written in an object oriented programming language such as Java, Smalltalk, C++ or the like. However, the computer program code for carrying out operations of the present disclosure may also be written in conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network/a wide area network/the Internet (e.g., network 14).

The present disclosure is described with reference to flowchart illustrations and/or block diagrams of methods, apparatus (systems) and computer program products according to embodiments of the disclosure. It will be understood that each block of the flowchart illustrations and/or block diagrams, and combinations of blocks in the flowchart illustrations and/or block diagrams, may be implemented by computer program instructions. These computer program instructions may be provided to a processor of a general purpose computer/special purpose computer/other programmable data processing apparatus, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

The flowcharts and block diagrams in the figures may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, not at all, or in any combination with any other flowcharts depending upon the functionality involved. It will also be noted that each block of the block diagrams and/or flowchart illustrations, and combinations of blocks in the block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

A number of implementations have been described. Having thus described the disclosure of the present application in detail and by reference to embodiments thereof, it will be apparent that modifications and variations are possible without departing from the scope of the disclosure defined in the appended claims.

What is claimed is:

1. A computer-implemented method, executed on a computing device, comprising:
   generating an obscured speech signal from an input speech signal and an obscured transcription from a transcription of the input speech signal, wherein the obscured speech signal and the obscured transcription include obscured representations of sensitive content from the input speech signal and the transcription of the input speech signal;
   extracting a speaker embedding from the input speech signal;
   generating a speaker embedding delta based upon, at least in part, the extracted speaker embedding and a synthetic speaker embedding;
   generating a synthetic speech signal from the obscured speech signal using the synthetic speaker embedding;
   generating a residual signal based upon, at least in part, the obscured speech signal and the speaker embedding delta; and
   training a speech processing system using the obscured transcription, the synthetic speech signal, the speaker embedding delta, and the residual signal.

2. The computer-implemented method of claim 1, wherein the sensitive content from the input speech signal and the transcription of the input speech signal includes personally identifiable information (PII) and/or protected health information (PHI).

3. The computer-implemented method of claim 1, wherein generating the residual signal includes:
   generating a resynthesized speech signal from the synthetic speech signal using the speaker embedding delta.

4. The computer-implemented method of claim 3, wherein generating the residual signal includes:
   generating the residual signal as the difference between the obscured speech signal and the resynthesized speech signal.

5. The computer-implemented method of claim 1, wherein training the speech processing system includes:
   generating a reconstructed speech signal using the synthetic speech signal, the speaker embedding delta, and the residual signal.

6. The computer-implemented method of claim 5, wherein training the speech processing system includes:
   training the speech processing system with the reconstructed speech signal and the obscured transcription.

7. The computer-implemented method of claim 1, wherein generating the obscured speech signal and the obscured transcription includes:
   marking each obscured representation of sensitive content in the obscured transcription, thus defining a plurality of obscured portion markings.

8. The computer-implemented method of claim 7, wherein training the speech processing system includes:
   training the speech processing system with a reconstructed speech signal, the obscured transcription, and the plurality of obscured portion markings.

9. A computing system comprising:
   a memory; and
   a processor configured to generate an obscured speech signal from an input speech signal and an obscured transcription from a transcription of the input speech signal, wherein the obscured speech signal and the obscured transcription include obscured representations of sensitive content from the input speech signal and the transcription of the input speech signal, wherein the processor is further configured to extract a speaker embedding from the input speech signal, wherein the processor is further configured to generate a speaker embedding delta based upon, at least in part, the extracted speaker embedding and a synthetic speaker embedding, wherein the processor is further configured to generate a synthetic speech signal from the obscured speech signal using the synthetic speaker embedding, wherein the processor is further configured to generate a residual signal based upon, at least in part, the obscured speech signal and the speaker embedding delta, and wherein the processor is further configured to train a speech processing system using the obscured transcription, the synthetic speech signal, the speaker embedding delta, and the residual signal.

10. The computing system of claim 9, wherein the sensitive content from the input speech signal and the transcription of the input speech signal includes personally identifiable information (PII) and/or protected health information (PHI).

11. The computing system of claim 9, wherein generating the residual signal includes:
    generating a resynthesized speech signal from the synthetic speech signal using the speaker embedding delta.

12. The computing system of claim 11, wherein generating the residual signal includes:

generating the residual signal as the difference between the obscured speech signal and the resynthesized speech signal.

13. The computing system of claim 9, wherein training the speech processing system includes:
    generating a reconstructed speech signal using the synthetic speech signal, the speaker embedding delta, and the residual signal.

14. The computing system of claim 12, wherein training the speech processing system includes:
    training the speech processing system with the reconstructed speech signal and the obscured transcription.

15. The computing system of claim 9, wherein generating the obscured speech signal and the obscured transcription includes:
    marking each obscured representation of sensitive content in the obscured transcription, thus defining a plurality of obscured portion markings.

16. A computer program product residing on a non-transitory computer readable medium having a plurality of instructions stored thereon which, when executed by a processor, cause the processor to perform operations comprising:
    generating an obscured speech signal from an input speech signal and an obscured transcription from a transcription of the input speech signal, wherein the obscured speech signal and the obscured transcription include obscured representations of sensitive content from the input speech signal and the transcription of the input speech signal;
    extracting a speaker embedding from the input speech signal;
    generating a speaker embedding delta based upon, at least in part, the extracted speaker embedding and a synthetic speaker embedding;
    generating a synthetic speech signal from the obscured speech signal using the synthetic speaker embedding;
    generating a resynthesized speech signal from the synthetic speech signal using the speaker embedding delta;
    generating a residual signal based upon, at least in part, the obscured speech signal and the resynthesized speech signal; and
    training a speech processing system using the obscured transcription, the synthetic speech signal, the speaker embedding delta, and the residual signal.

17. The computer program product of claim 16, wherein the sensitive content from the input speech signal and the transcription of the input speech signal includes personally identifiable information (PII) and/or protected health information (PHI).

18. The computer program product of claim 16, wherein training the speech processing system includes:
    generating a reconstructed speech signal using the synthetic speech signal, the speaker embedding delta, and the residual signal.

19. The computer program product of claim 18, wherein training the speech processing system includes:
    training the speech processing system with the reconstructed speech signal and the obscured transcription.

20. The computer program product of claim 16, wherein generating the obscured speech signal and the obscured transcription includes:
    marking each obscured representation of sensitive content in the obscured transcription, thus defining a plurality of obscured portion markings.

* * * * *